United States Patent [19]
Abidin et al.

[11] Patent Number: 5,662,221
[45] Date of Patent: *Sep. 2, 1997

[54] LOW-COST SAFE BLADE PACKAGE FOR SURGICAL PURPOSES

[75] Inventors: Michael R. Abidin, Birmingham, Ala.; Steven P. Lehmbeck, Baltimore, Md.

[73] Assignee: Bloom & Kreten, Towson, Md.; a part interest

[*] Notice: The portion of the term of this patent subsequent to May 18, 2014, has been disclaimed.

[21] Appl. No.: 547,685

[22] Filed: Oct. 19, 1995

Related U.S. Application Data

[60] Continuation-in-part of Ser. No. 435,668, May 5, 1995, Pat. No. 5,528,811, which is a division of Ser. No. 245,009, May 18, 1994, Pat. No. 5,433,321.

[51] Int. Cl.⁶ .................................................. B65D 85/00
[52] U.S. Cl. .................................... 206/354; 206/352
[58] Field of Search ........................... 206/352–360, 206/363–365, 438, 439

[56] References Cited

U.S. PATENT DOCUMENTS

| | | | |
|---|---|---|---|
| 1,167,464 | 1/1916 | Young . | |
| 1,448,305 | 3/1923 | Langbein | 30/339 |
| 1,608,274 | 11/1926 | Grayson . | |
| 2,131,358 | 9/1938 | Rothschild | 30/125 |
| 2,866,542 | 12/1958 | Svirchev | 206/63.2 |
| 3,447,181 | 6/1969 | Coker et al. | 15/104.94 |
| 3,543,918 | 12/1970 | Waterman | 206/16 |
| 4,095,691 | 6/1978 | Iten | 206/354 |
| 4,106,620 | 8/1978 | Brimmer et al. | 206/363 |
| 4,120,397 | 10/1978 | Neumann | 206/370 |
| 4,157,758 | 6/1979 | Kozlowski, Jr. | 206/363 |
| 4,180,162 | 12/1979 | Magney | 206/363 |
| 4,270,416 | 6/1981 | Thompson | 81/3 R |
| 4,344,532 | 8/1982 | Eldridge, Jr. et al. | 206/370 |
| 4,395,807 | 8/1983 | Eldridge, Jr. et al. | 29/239 |
| 4,523,679 | 6/1985 | Paikoff et al. | 206/370 |
| 4,730,376 | 3/1988 | Yamada | 29/239 |
| 4,736,842 | 4/1988 | Uetake et al. | 206/363 |
| 4,746,016 | 5/1988 | Pollak et al. | 206/356 |
| 4,903,390 | 2/1990 | Vidal et al. | 29/239 |
| 4,998,334 | 3/1991 | Pemberton et al. | 206/359 |
| 5,088,173 | 2/1992 | Kromer et al. | 206/370 |
| 5,301,807 | 4/1994 | Donahue | 206/370 |
| 5,361,902 | 11/1994 | Abidin et al. | 206/370 |
| 5,363,958 | 11/1994 | Horan | 206/356 |
| 5,433,321 | 7/1995 | Abidin et al. | 206/354 |

OTHER PUBLICATIONS

Photocopies (front and back) of product packaging for "X-ACTO" No. 11 Fine Point Blade Safety Dispenser.

*Primary Examiner*—Jimmy G. Foster
*Attorney, Agent, or Firm*—Leonard Bloom

[57] ABSTRACT

A blade package for a surgical scalpel includes a base supporting a blade and retaining the blade against movement in the package, thereby preventing inadvertent dulling of the blade, and a thin film is bonded to the base and covers the blade. This film has a tab for rupturing the film and tearing it away from the base, thereby exposing the blade for subsequent mounting on to the scalpel handle. Preferably, the film is transparent, so that the blade is visible within the blade package.

14 Claims, 9 Drawing Sheets

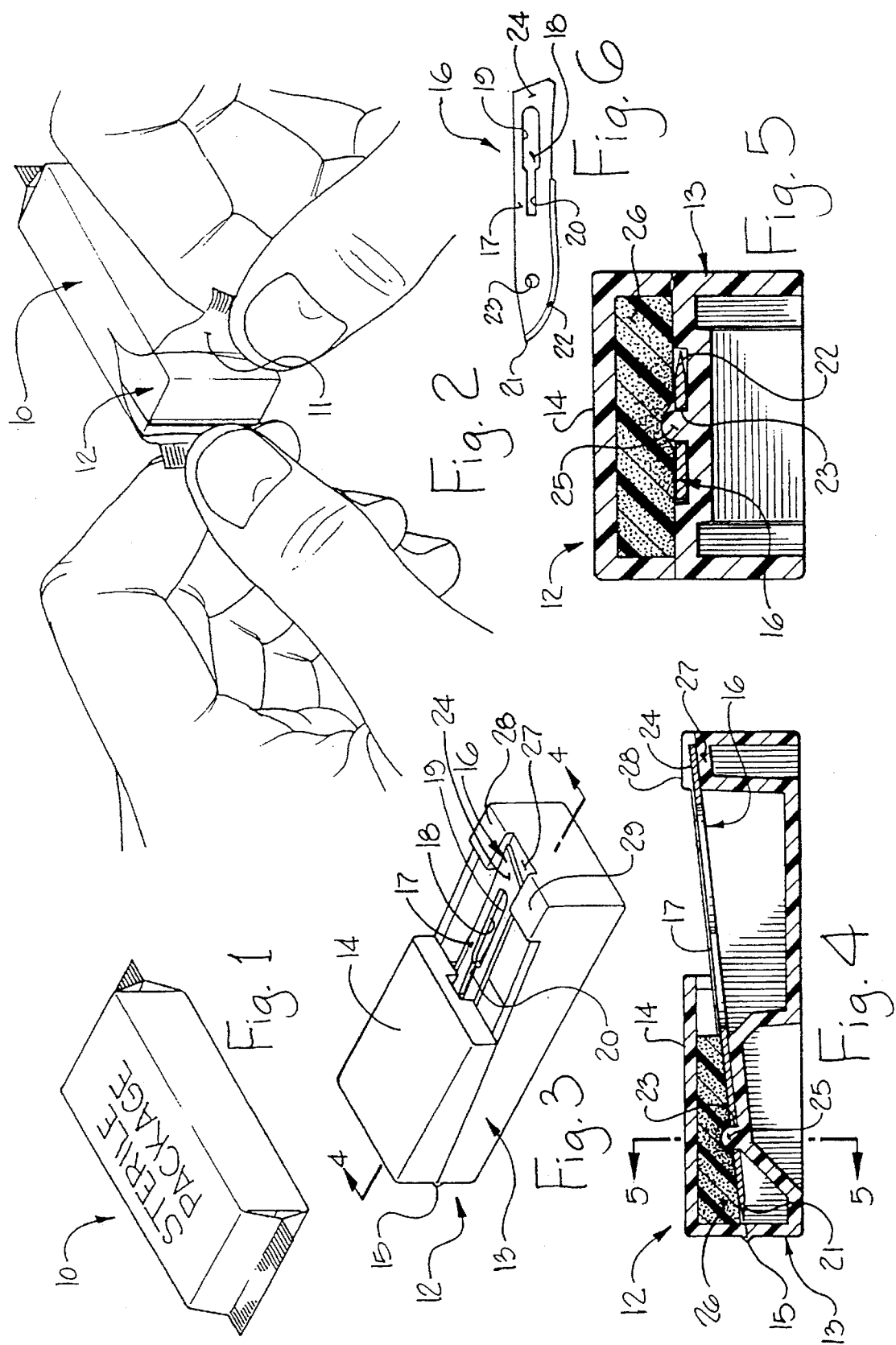

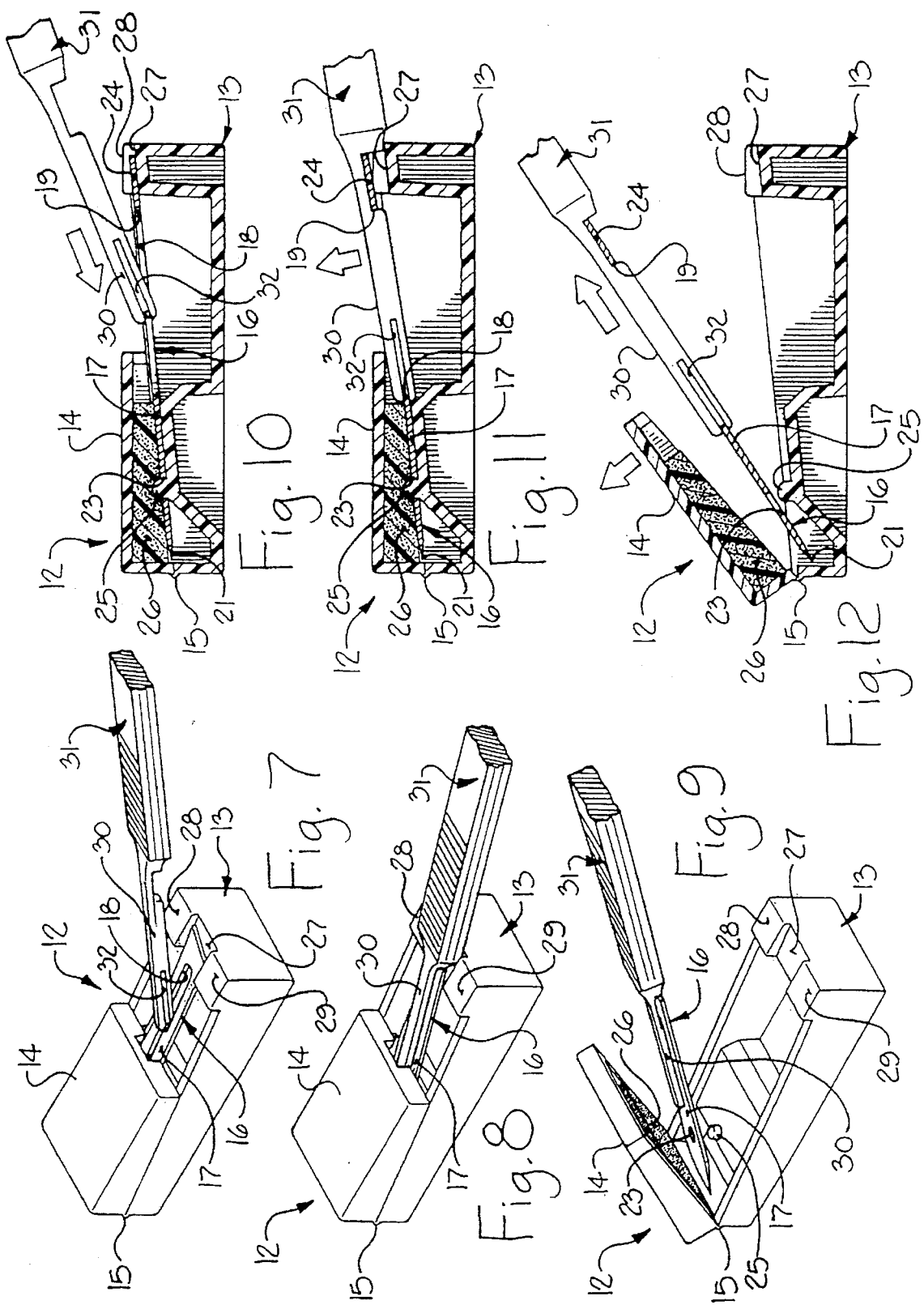

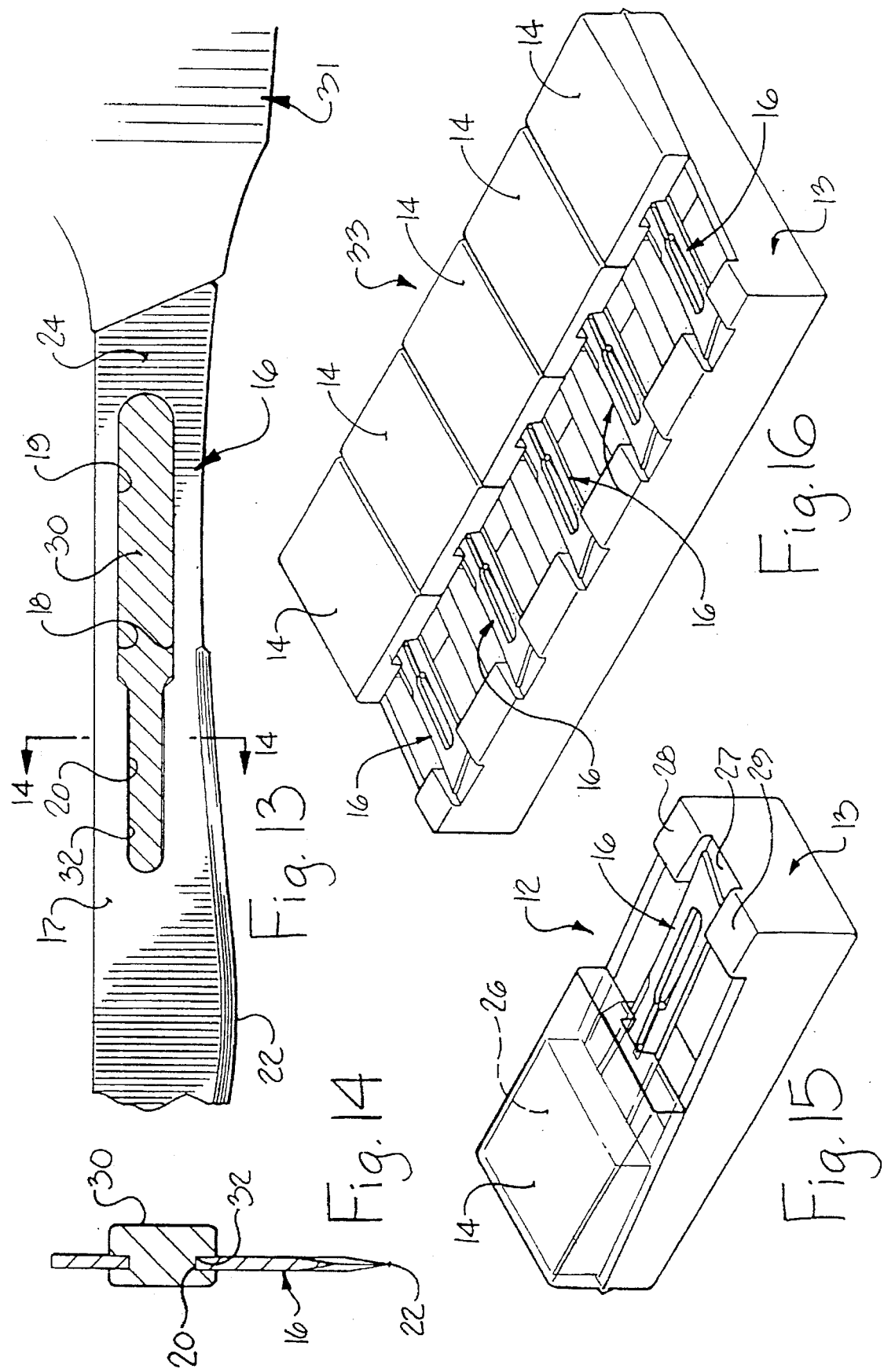

LOW-COST SAFE BLADE PACKAGE FOR SURGICAL PURPOSES

CROSS REFERENCE TO RELATED APPLICATIONS

The present invention is a continuation-in-part of application Ser. No. 08/435,668 filed May 5, 1995, U.S. Pat. No. 5,528,811, which, in turn, is a division of application Ser. No. 245,009 filed May 18, 1994 (the latter application having issued on Jul. 18, 1995 as U.S. Pat. No. 5,433,321.

STATEMENT REGARDING FEDERALLY SPONSORED RESEARCH OR DEVELOPMENT (Not applicable.)

REFERENCE TO A MICROFICHE APENDIX SPECIFYING THE TOTAL NUMBER OF MICROFICHE AND TOTAL NUMBER OF FRAMES (Not applicable.)

BACKGROUND OF THE INVENTION

The present invention relates to a package for a surgical scalpel blade and, more particularly, to a blade package for safely mounting the blade on a forwardly-extending cleat on the scalpel.

Surgical scalpel blades are usually packaged individually in an aluminum foil wrap and are irradiated for sterilization purposes. The sterile foil wrap is torn open in the operating room ("O.R.") in a hospital or clinic, and the blade is removed and mounted on a surgical scalpel. The scalpel has a forwardly-projecting portion (referred to in the art as a "cleat") and this cleat is inserted within a longitudinal closed slot formed in the blade, thereby mounting the blade on the scalpel. The blade is relatively thin and flexible, the cleat on the scalpel has a groove to receive the blade, and the mounting is with a slight "snap" fit or "click".

Some scalpel blades, which are used in microsurgery, are super sharp and are packaged in a molded plastic package consisting of a base and a pivoted cover.

The scalpel blades are usually changed several times during a medical procedure in the O.R., since it is imperative that the sharpness of the blades be maintained. The blades are usually changed by a nurse or O.R. technician (called the "tech").

Whether the blade is packaged in an aluminum foil or in a molded plastic package, the blade is removed therefrom; and during the blade mounting process, the tech holds the scalpel in one hand and the blade in the other hand and slips the blade on to the cleat on the scalpel. These blades are roughly an inch to an inch-and-a-half long and (of course) are razor sharp, so it is not at all uncommon for the tech to be nicked or cut while mounting one of the blades, thereby causing blood flow.

If the patient is H.I.V.-infected, the tech may sero-convert and become H.I.V.-infected leading to the deadly AIDS disease. Conversely, if the tech is an H.I.V. carrier, the patient or the other health care providers in the O.R. are at risk. The same is true with respect to hepatitis or other infectious diseases.

The nurse or tech is very often under intense pressure in the O.R. and may become temporarily distracted while in the process of changing blades. This tends to aggravate the existing problem.

BRIEF SUMMARY OF THE INVENTION

Accordingly, it is an object of the present invention to provide a safety blade package for a surgical scalpel, thereby avoiding cuts or nicks when installing a new blade on the scalpel.

It is another object of the present invention to provide a safety blade package that may be manufactured conveniently and at relatively low cost, thereby facilitating widespread marketing and distribution.

It is yet another object of the present invention to provide a safety blade package that is "user friendly" so that the hospital nurses and O.R. techs will immediately understand the use thereof and will readily appreciate its ease, convenience and safety features.

In accordance with the teachings of the present invention, a blade package for safely mounting a blade on a surgical scalpel is herein disclosed and claimed, wherein the blade includes a cutting edge and further includes a body portion having a slot formed therein, the body portion having a rear end portion, and wherein the scalpel has a forwardly-projecting cleat received within the slot in the blade. The blade package includes a base having a ledge supporting the rear end portion of the blade. The blade further has a hole formed therein; and the base further has an upstanding pin received in the hole in the blade, thereby mounting the blade on the base and preventing substantial movement of the blade within the package, and thereby preventing any inadvertent dulling of the cutting edge on the blade. As a result, the cleat on the scalpel may be inserted within the slot on the blade; and the scalpel with the blade mounted thereon may be lifted up and away from the base, thereby clearing the hole in the blade from the pin on the base.

Preferably, a cover is pivotably mounted on the base. The cover has a pivot axis which is substantially perpendicular to the pin and spaced therefrom; and the cover extends partially over the base, substantially covering the cutting edge of the blade, and exposing the slot formed within the blade, such that the cover is pivoted away from the base as the scalpel with the blade thereon is lifted away from the base.

In a preferred embodiment, the cover is transparent, such that the cutting edge on the blade is visible through the cover; and the cover carries a cushion bearing against the blade.

The ledge on the base supporting the rear end portion of the blade is canted downwardly in a direction towards the pin, such that the blade is inclined with respect to the base, thereby facilitating the insertion of the cleat on the scalpel into the slot on the blade. Preferably, the base is provided with a pair of spaced-apart raised lands, one on each side of the ledge on the base.

The present invention also provides an improved surgical blade comprising a main body portion having an elongated slot formed therein, a tip and a cutting edge, the elongated slot having a narrowed forward portion, and a hole formed in the blade between the tip and the narrowed forward portion of the elongated slot.

Viewed in another aspect, the present invention provides an improved method of mounting a blade on a surgical scalpel, wherein the scalpel has a forwardly-extending cleat. A sterile blade package is opened to obtain a blade package assembly; and this blade package assembly includes a base having a blade mounted thereon. The blade has a main body portion provided with a longitudinal slot, and the blade further has a tip and a cutting edge. The base is provided with a pivoted cover covering at least the tip of the blade.

The cleat on the scalpel is inserted into the longitudinal slot in the blade, so that the blade is "snapped" on to the cleat; and the scalpel with the blade mounted thereon is moved up and away from the base to lift the cover and pivot it away from the base, thereby clearing the scalpel with the blade thereon from the blade package assembly.

In accordance with the further teachings of the present invention, there is herein disclosed a blade package for a blade used for surgical purposes, wherein the blade is intended to be mounted on the cleat of a scalpel handle, and wherein the blade is provided with a slot having a forward portion and is further provided with a tip and a cutting edge. This blade package includes a base, and means are provided on the base for supporting the blade and assuring that the cutting edge on the blade will not become dulled by inadvertent contact with the base during shipment, storage or handling of the blade package. A relatively-thin film is secured to the base and covers the blade; and this film is provided with at least a frangible portion, such that the film may be torn away or lifted up and away from the base to expose the blade. Thereafter, the cleat on the scalpel handle may be inserted into the slot in the blade to mount the blade on the scalpel handle, and the blade thus mounted on the scalpel handle may be lifted out of the base of the blade package. The blade package is then discarded.

Preferably, the means on the base for supporting the blade and assuring that the cutting edge on the blade will not become dulled by inadvertent contact with the base during shipment, storage or handling of the blade package, comprises an upstanding pin on the base; and the blade has a hole formed therein to receive the pin.

Preferably, the hole in the blade is disposed between the tip of the blade and the forward portion of the slot in the blade.

Moreover, the base has a rear end wall having a notch formed therein, and the blade further has a rear portion received within the notch.

In a preferred embodiment, an interference fit is provided between the pin and the hole, and between the notch and the rear portion of the blade, respectively, such that the blade is received on the base with a "snap" fit.

The film is transparent, preferably, so that the blade is visible in the blade package; and a tab is provided on the film, such that the tab may be gripped to rupture the frangible portion of the film and lift the film up and away from the base, thereby providing access to the blade.

The base has a peripheral rim, the blade is disposed on the base below the rim, and the base has a bottom wall formed with an elevated cored-out portion supporting the pin.

Preferably, the base has respective sides which are indented concavely therein and provided with respective serrations, thereby facilitating gripping of the base.

These and other objects of the present invention will become apparent from a reading of the following specification taken in conjunction with the enclosed drawings.

BRIEF DESCRIPTION OF THE DRAWINGS

FIG. 1 is a pictorial view of a sterile blade package protected by a removable foil.

FIG. 2 is a further pictorial view, corresponding to FIG. 1, but showing the foil being removed for access to the blade package assembly of the present invention.

FIG. 3 is a perspective view of the blade package assembly including a base, a blade mounted on the base, and a partial cover pivotably mounted on the base for protecting the blade.

FIG. 4 is a cross-sectional view thereof, taken along the lines 4—4 of FIG. 3 and drawn to an enlarged scale, and showing an upstanding pin on the base, the pin being received within a hole in the blade, and further showing the rear end portion of the blade supported upon a ledge on the base, the blade preferably being inclined downwardly towards the pin.

FIG. 5 is a cross-sectional view thereof, taken along the lines 5—5 of FIG. 4 and showing how the cutting edge of the blade is maintained in a spaced relationship at all times with the blade package assembly, thereby precluding the blade from being dulled inadvertently.

FIG. 6 is a plan outline of the improved blade of the present invention.

FIG. 7 is a pictorial view showing the cleat on the scalpel initially being inserted into the slot on the blade.

FIG. 8 is a further pictorial view, corresponding substantially to FIG. 7, but showing the cleat on the scalpel fully seated within the slot on the blade.

FIG. 9 is a still further pictorial view, corresponding substantially to FIG. 8, but showing the scalpel (with the blade mounted thereon) being lifted up and away from the base, thereby pivoting the cover, and thereby clearing the hole in the blade from the pin on the base.

FIGS. 10–12 are schematic sequence views, corresponding to FIGS. 7–9, respectively, and showing how the blade may be safely and easily mounted on the scalpel in a matter of seconds.

FIG. 13 is a cross-sectional view, taken along the lines 13—13 of FIG. 12 and drawn to an enlarged scale, and showing the detailed construction of the slot in the blade and the cleat on the scalpel.

FIG. 14 is a cross-sectional view thereof, taken along the lines 14—14 of FIG. 13.

FIG. 15 is a pictorial view of a portion of FIG. 3, showing the cover as preferably transparent.

FIG. 16 is a further pictorial view, showing how a plurality of blades may be packaged in a single blade package, the package facilitating individual blade selection and mounting.

DESCRIPTION

Figure 17:
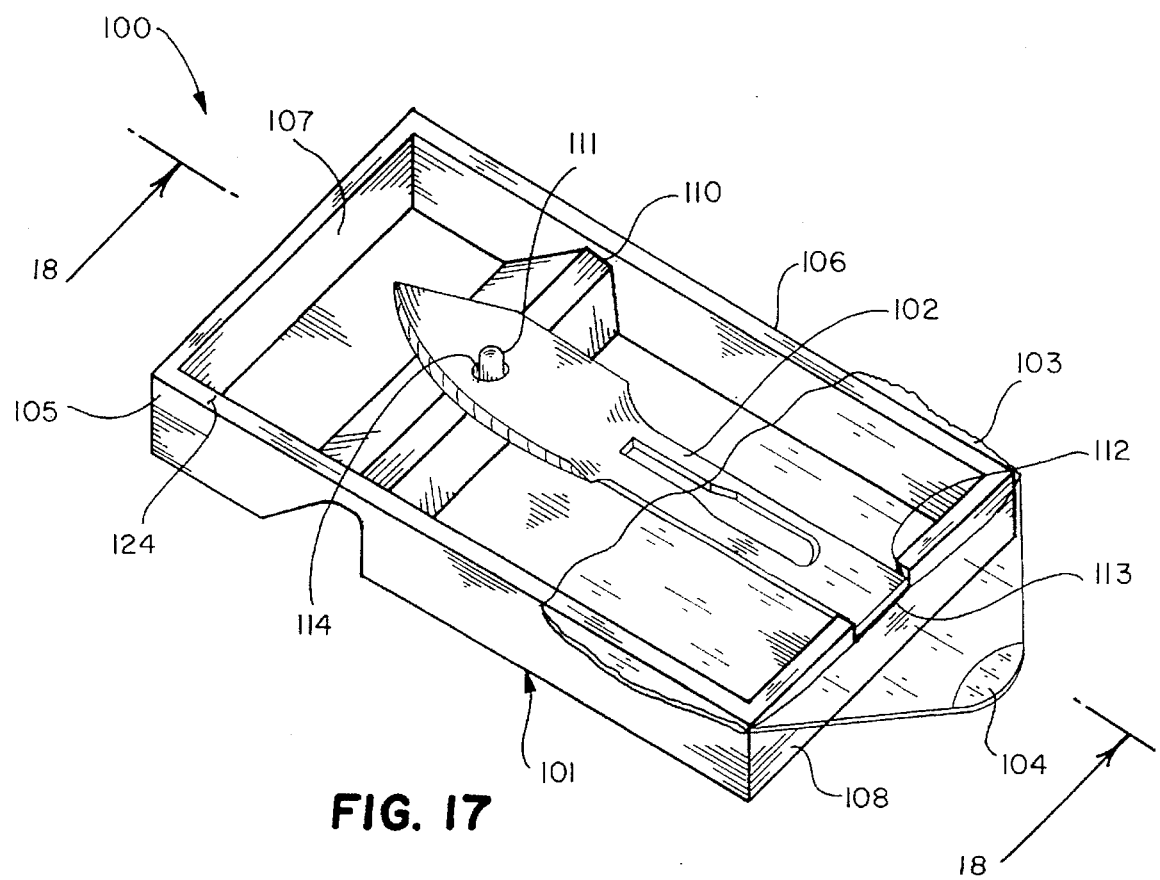
FIG. 17 is a perspective view of another embodiment of the blade package of the present invention, showing a frangible film bonded to the base of the blade package, the film being partially torn away to show a portion of the blade mounted on the base, and the film having a tab projecting rearwardly of the package for tearing off the film from the base of the package.

With reference to FIGS. 1–3, a sterile blade package 10 (FIG. 1) is wrapped in an aluminum foil 11 which is torn open (FIG. 2) in the O.R. (or other medical or hospital environment) to obtain the blade package assembly 12 of the present invention (FIG. 3).

With further reference to FIGS. 4 and 5, the blade package assembly 12 preferably comprises a single molded article and includes a base 13 and a cover 14 pivoted thereto by means of an integral reduced cross-section "living" hinge 15. The cover 14 extends partially over the base 13 and, preferably, the cover 14 is transparent (FIG. 15) along with the blade package assembly 12.

A blade 16 is mounted on the base 13. As shown more clearly in FIG. 6, the blade 16 has a main body portion 17 provided with a longitudinal slot 18. This slot 18 includes a rearward portion 19 and a narrowed forward portion 20. The blade 16 further has a tip 21, a bottom cutting edge 22, a hole 23 between the tip 21 and the slot 20, and a rear end portion 24 beyond the slot 20.

The base 13 has an upstanding pin 25 which is substantially perpendicular to the pivot axis of the cover 14 and spaced therefrom. This pin 25 is received in the hole 23 in the blade 16, thereby positioning the blade 16 on the base 13. The cover 14, in turn, is provided with a cushioned pad 26 of foam plastic (or other suitable material) to trap the blade 16 between the base 13 and the cover 14.

The base 13 further has a ledge 27 supporting the rear end portion 24 of the blade 16. Preferably, the ledge 27 is elevated so that the blade 16 is canted downwardly, as shown more clearly in FIG. 4. The base 13 further has a pair of spaced-apart raised lands 28 and 29, respectively, one on each side of the ledge 27.

This arrangement prevents undesired movement of the blade 16 (which would otherwise inadvertently dull the cutting edge 22 of the blade 16).

The operation of the invention and its inherent features and advantages are illustrated in FIGS. 7–12, respectively.

The blade 16 is mounted on the forwardly-extending cleat 30 of a surgical scalpel 31. Preferably (but not necessarily) the scalpel 31 is a guarded surgical scalpel as disclosed and claimed in U.S. Pat. No. 5,250,063 issued Oct. 5, 1993 and No. 5,275,606 issued Jan. 4, 1994 to the present inventors (applicants). It will be appreciated by those skilled in the art, however, that the present invention is equally applicable to conventional non-guarded scalpels, if desired.

As shown more clearly in FIGS. 7 and 10, the cleat 30 on the scalpel 31 is initially inserted into the rearward portion 19 of the slot 18 in the blade 16. The cleat 30 is then advanced forwardly such that the cleat 30 is fully seated within the slot 18 (which may be with a slight "click" or "snap" fit) as shown more clearly in FIGS. 8 and 11. Thereafter, the scalpel 31 with the blade 16 mounted thereon is lifted up and away from the base 13 (FIGS. 9 and 12) to pivot the cover 14 away from the base 13 and, more significantly, to clear the hole 23 in the blade 16 from the pin 25 on the base 13.

The entire operation of thus mounting the blade 16 on the scalpel 31 is easy and convenient, takes only a few seconds, and assures that the user will not be cut or nicked accidentally.

With reference to FIGS. 13 and 14, the cleat 30 on the scalpel 31 has a groove 32 formed therein to receive the slot 18 on the blade 16. These blades 16 are in widespread use in hospitals and clinics. However, it will be appreciated by those skilled in the art that the present invention is not necessarily confined thereto but, rather, is equally applicable to other surgical blade designs and configurations.

With reference to FIG. 16, the teachings of the present invention are equally applicable to a multi-blade package 33 having a plurality of blades 16 in a side-by-side relationship therein. This multi-blade package 33 would be contained in a single sterile package (not shown) which would be opened in the O.R.

The surgical scalpel blades 16 are razor sharp and can become dulled very quickly during a surgical procedure. It is important for the surgeon to have a very sharp "fresh" blade readily available. During a typical operation, the blades 16 may be changed around a half dozen times. This invention assures that the blades 16 may be quickly, easily and safely mounted on the scalpel 31 during the surgical procedure.

Moreover, it is significant that the blade does not move during the mounting process (unlike the prior art razor blade dispensers and injectors) and that the mounting of the blade involves basically two steps: first, insertion of the scalpel and, second, lifting of the scalpel (with the blade thereon) to pivot the cover and clear the blade package assembly. This movement is foolproof, convenient, safe, takes only a few seconds, and is readily understood by the O.R. techs, assistants and surgeons.

As disclosed herein, the mounting of the blade on the scalpel is basically a two-hand operation: one hand holding the blade package assembly 12, and the other hand holding the scalpel 31. However, if desired, a ledge or suitable mounting may be provided on the tray table (not shown) for retaining the blade package assembly 12, so that only the scalpel 31 is held. This is a one-hand operation.

Figure 18:
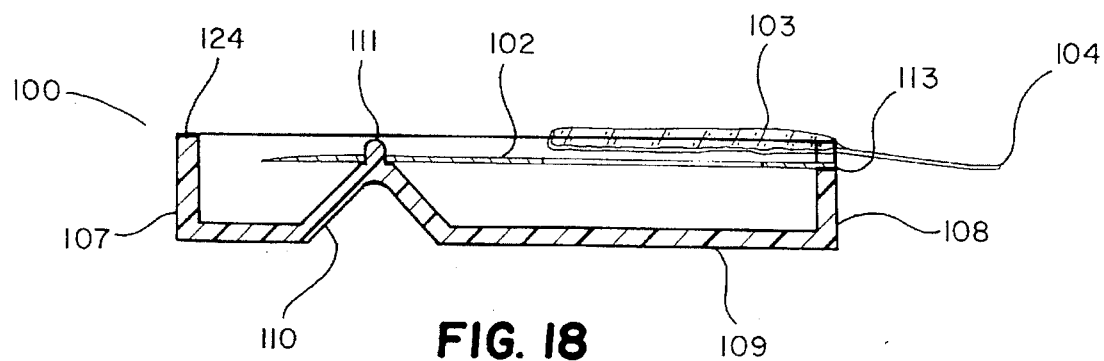
FIG. 18 is a longitudinal section view thereof, taken along the lines 18—18 of FIG. 17.

With reference to FIGS. 17 and 18, the blade package 100 includes a base 101 supporting a blade 102, and a thin film 103 covers the blade 102 and is bonded to the base 101 by a suitable known method, such as heat sealing or ultrasonic welding. The film 103 is of polyethylene (or other suitable material) and, preferably, is transparent so that the blade 102 is visible in the package 100. The package 100, with the blade 102 therein, can be sterilized by radiation or by gas (ethylene oxide) depending upon manufacturing preferences.

The film 103 has at least a frangible portion and, preferably, a tab 104 is formed integrally with the film 103 to facilitate rupturing or peeling off the film 103 and lifting it up and away from the base 101. In this embodiment of the invention, the tab 104 projects rearwardly of the base 101 and has a substantially triangular plan outline; however, other plan outlines of the tab 104, as well as other means for tearing off or rupturing the film 103, are feasible consonant with the teachings of the present invention.

Figure 19:
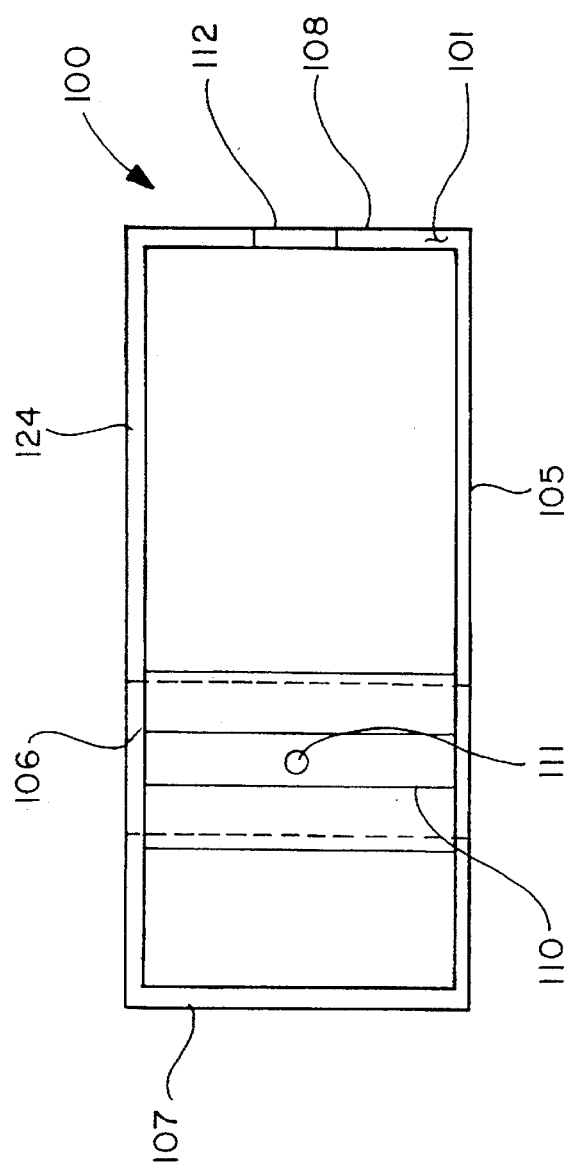
FIG. 19 is a top plan view of the base only.
Figure 21:
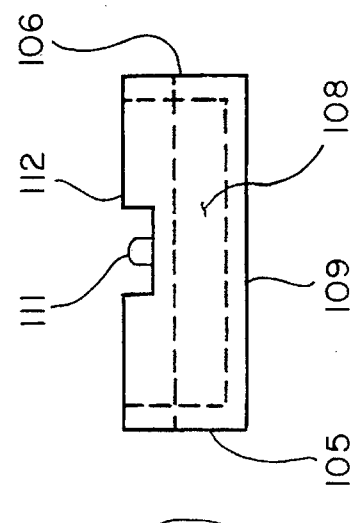
FIG. 21 is an end view thereof.
Figure 20:
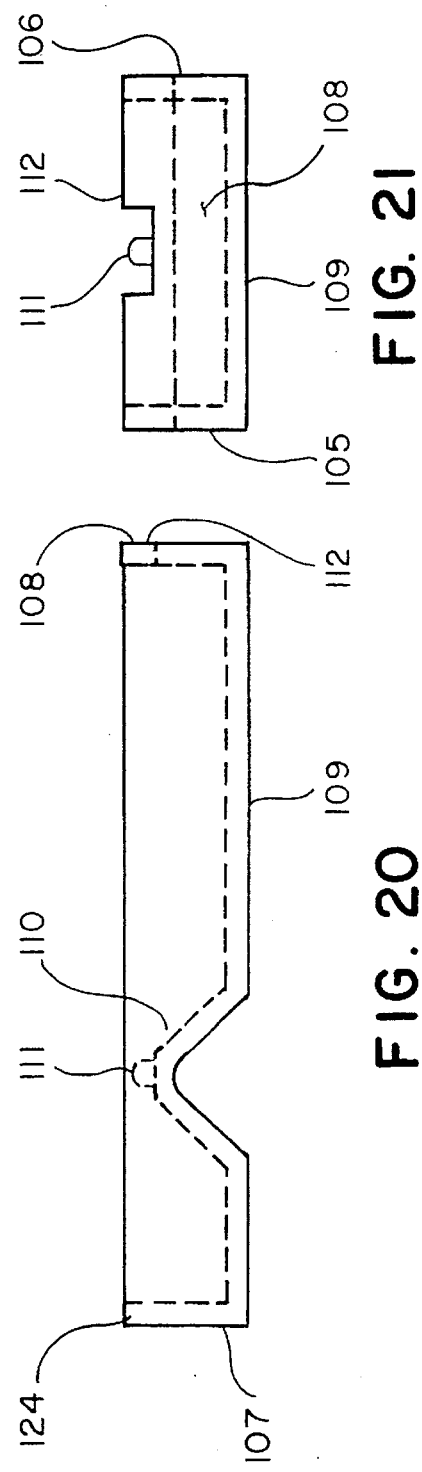
FIG. 20 is a side elevation view thereof.

With reference to FIGS. 19–21, the base 101 is substantially rectangular or obling (although other shapes are possible) and has side walls 105, 106 and end walls 107, 108, respectively, and a bottom wall 109. The bottom wall 109 has an upstanding portion 110 (which, preferably, is cored out to reduce material) and is provided with an upstanding integrally-formed pin 111; and the end wall 108 of the base 101 has a notch 112 formed therein.

The blade 102 has a rear portion 113 received in the notch 112 formed in the end wall 108 of the base 101, and the blade 102 further has a hole 114 formed therein to receive the pin 111 on the base 101, as shown more clearly in FIGS. 17 and 18. Preferably, the blade 102 is substantially "straight" on the base 101, that is, substantially parallel to the bottom wall 109, as shown in FIG. 18, although the blade 102 may be slightly inclined in the package 100 (if desired).

Figure 22:
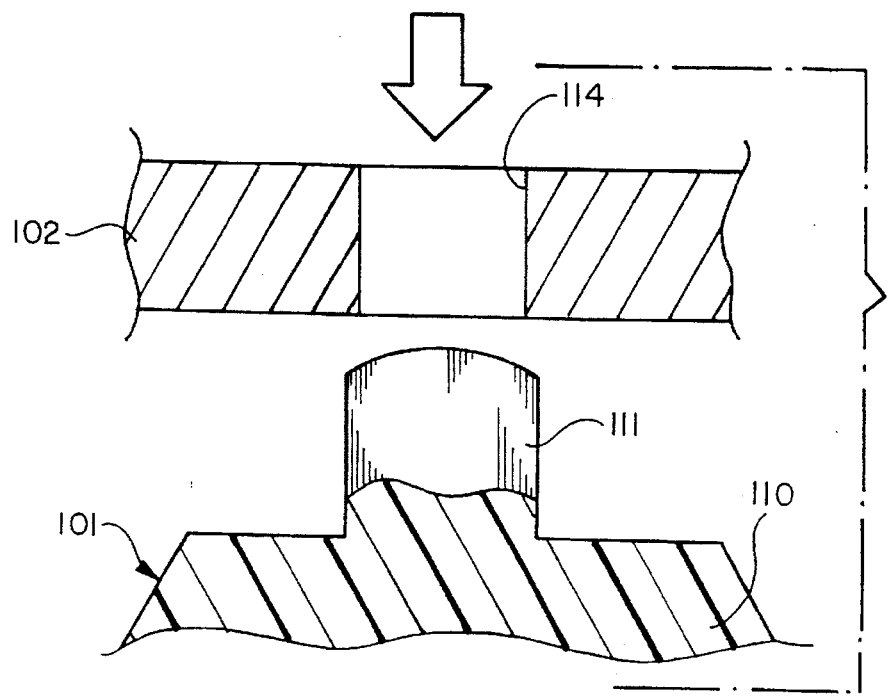
FIGS. 22 and 23 are schematic sequence views, drawn to an enlarged scale, and showing the hole in the blade being received over the pin on the base with a slight interference fit.
Figure 23:
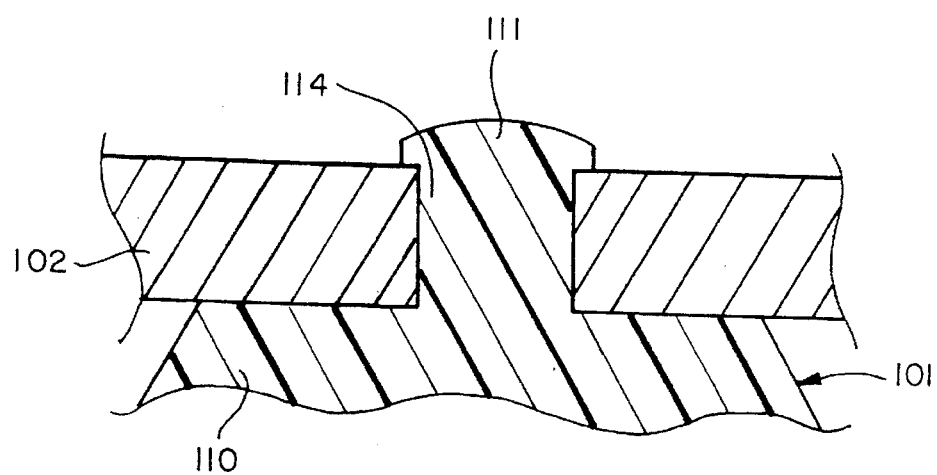
Figure 24:
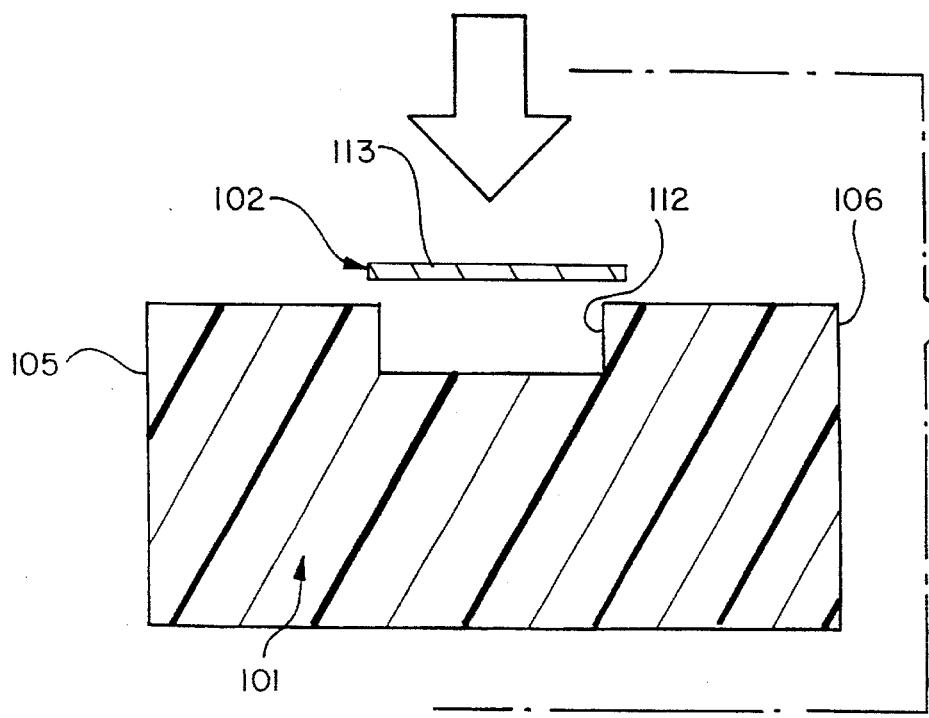
FIGS. 24 and 25 are further schematic sequence views, drawn to an enlarged scale, and showing the rear portion of the blade being received in the notch of the rear end wall on the base with a slight interference fit.
Figure 25:
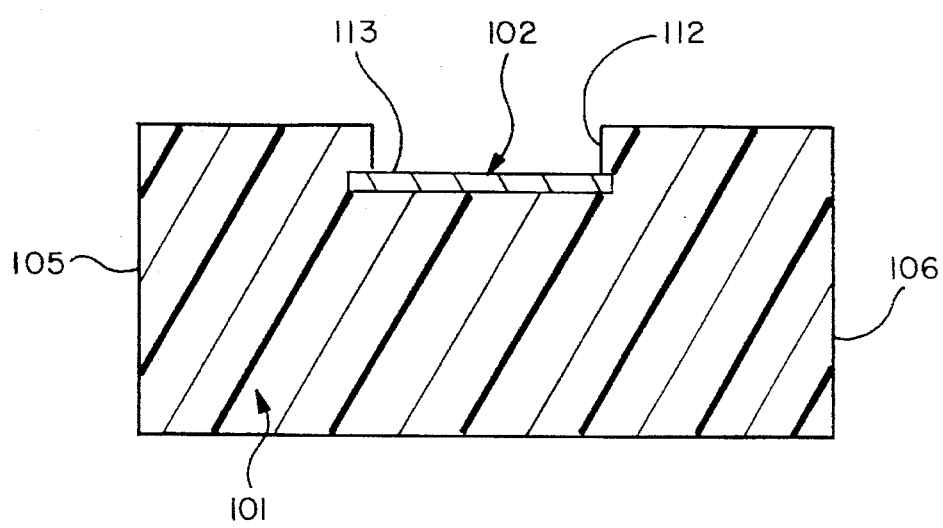

With reference to FIGS. 22 and 23, the diameter of the pin 111 is greater than the diameter of the hole 114 in the blade 102, such that the pin 111 is received in the hole 114 with a slight press-fit or interference fit. Also, with reference to FIGS. 24 and 25, the rear portion 113 of the blade 102 is received in the notch 102 in the end wall 108 with a slight press-fit or interference fit. The plastic material of the base 101 is thereby distorted, somewhat, as the blade 102 is "popped" into the base 101 with a "snap" fit during the manufacturing process.

Figure 26:
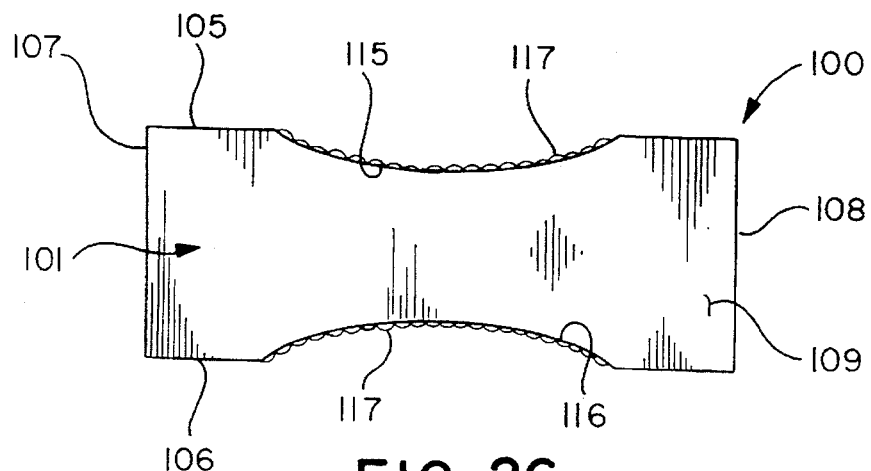
FIG. 26 is a top plan view of a modified base, wherein the sides of the base are indented concavely to facilitate gripping the base between the thumb and forefinger.
Figure 27:
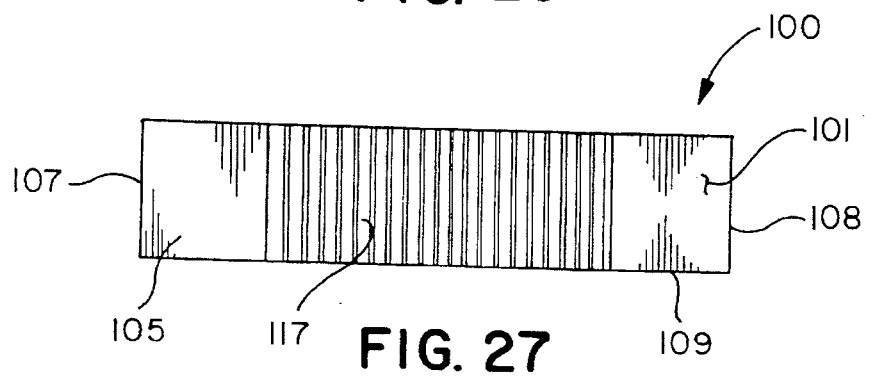
FIG. 27 is a side elevation thereof, showing serrations or grooves on the concave indents to facilitate gripping.

With reference to FIGS. 26 and 27, the respective side walls 105 and 106 of the base 101 are indented concavely (FIG. 26) and these concave indents 115 and 116, respectively, are preferably formed with serrations or parallel grooves 117 (FIG. 27) to facilitate gripping the base 101 between the thumb and forefinger as the tab 104 is pulled to rupture the frangible film 103 and lift it up and away from the base 101.

Thereafter, the blade 102 may be mounted on the scalpel handle in a manner similar to the embodiment of FIGS. 7–12 and, it will be appreciated, the leverage exerted by the scalpel handle will cause the blade 102 to "pop" out of the base 101 of the package 100.

The base 101 is a simple, lightweight low-cost molded plastic piece; and the mold for the base 101 will not have any "side pulls", thereby reducing the mold costs and the cycle time.

Figure 28:
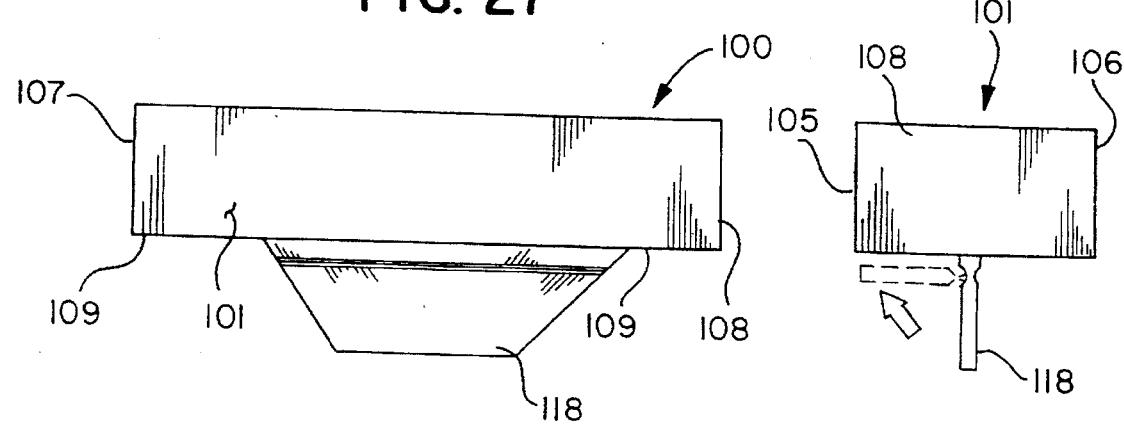
FIG. 28 is a further modification of the base, showing a depending panel for alternate gripping of the base.
Figure 29:
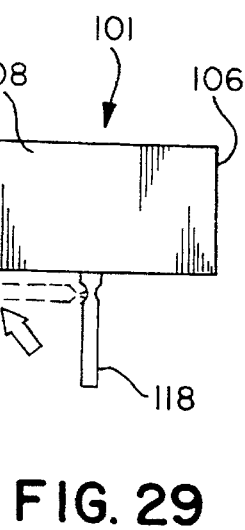
FIG. 29 is an end view thereof, showing the depending panel joined to the base by a "living" hinge for compactness of the blade package in shipment and storage.

With reference to FIGS. 28 and 29, the base 101 may have a depending panel 118 for gripping purposes, if desired. If so, the panel 118 may be joined to the base 101 by a "living" hinge 119, so that the panel 118 may be folded up against the base for compactness in shipping and storage.

Figure 30:
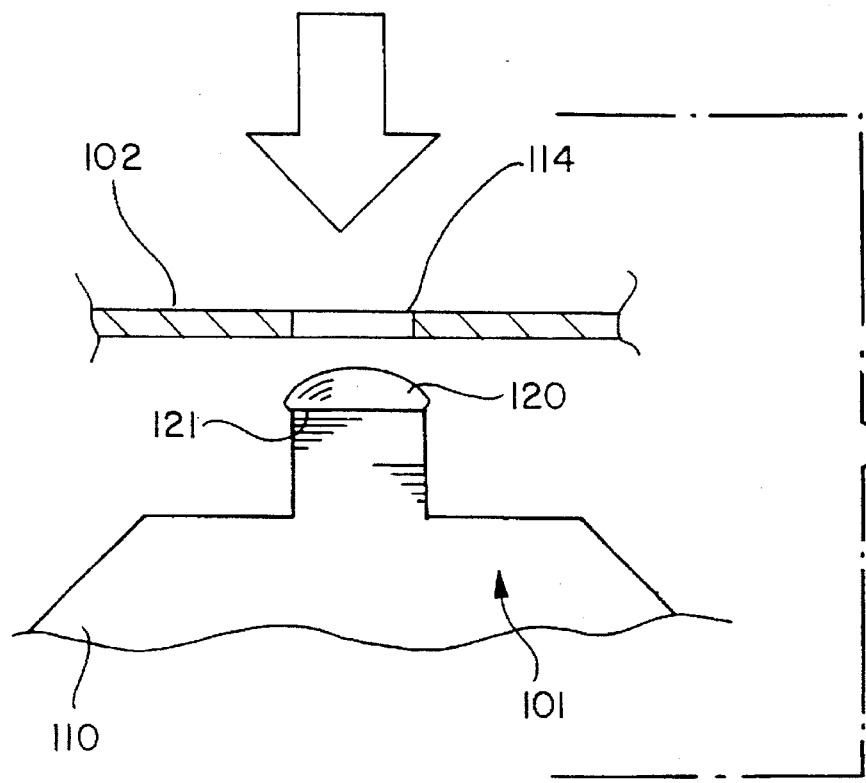
FIG. 30 is a modification of the pin on the base, showing a "mushroom" cap on the pin, thereby facilitating a "snap" fit.
Figure 31:
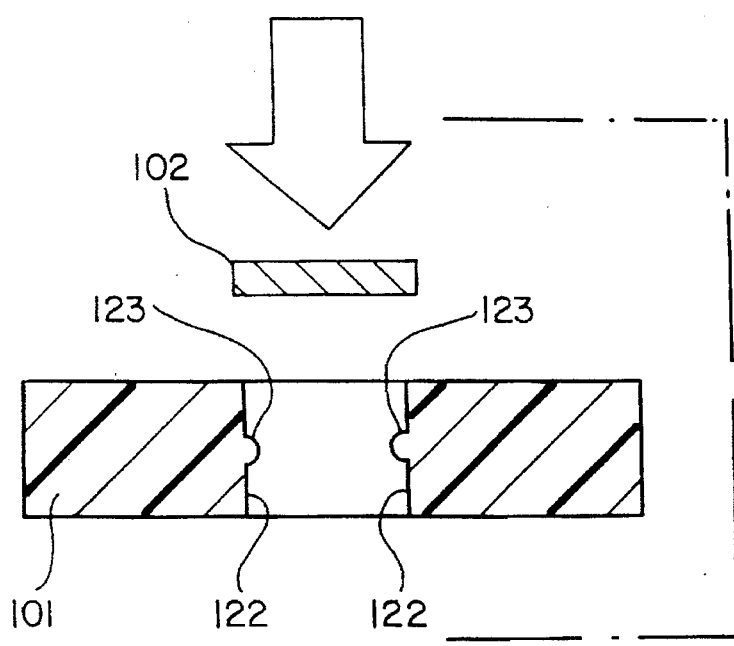
FIG. 31 is a modification of the notch on the base, showing respective protrusions to facilitate receipt of the base with a "snap" fit.

With reference to FIG. 30, and again if desired, the pin 111 may have a "mushroom" cap 120 providing an annular shoulder 121, and with reference to FIG. 31, the sides 122 of the notch 112 may have protrusions or ridges 123, to improve the interference fit.

With reference again to FIG. 18, the blade 102 is disposed below the peripheral rim 124 of the base 101.

It will be appreciated by those skilled in the art that the blade packages of the present invention are substantially safer, more convenient and easier to use, and readily sterilizable. Moreover, the blade packages of the present invention are less expensive to manufacture. This is particularly the case with the improved blade package of FIGS. 18–27, wherein the base is a simple low-cost moldment requiring no side pulls, the blade is snapped into the base and is retained therein against movement, and the film is disposed over the blade and is readily bonded to the base. This film is transparent so that the blade is visible at all times.

Obviously, many modifications may be made without departing from the basic spirit of the present invention.

Accordingly, it will be appreciated by those skilled in the art that within the scope of the appended claims, the invention may be practiced other than has been specifically described herein.

We claim:

1. A blade package for a blade used for surgical purposes, wherein the blade is intended to be mounted on the cleat of a scalpel handle, and wherein the blade is provided with a slot having a forward portion and is further provided with a tip and a cutting edge, comprising a base, means on the base for supporting the blade and assuring that the cutting edge on the blade will not become dulled by inadvertent contact with the base during shipment, storage or handling of the blade package, and a relatively-thin film secured to the base and covering the blade, the film being provided with at least a frangible portion, such that the film may be torn away or lifted up and away from the base to expose the blade, such that the cleat on the scalpel handle may be inserted into the slot in the blade to mount the blade on the scalpel handle, and such that the blade mounted on the scalpel handle may be lifted out of the base of the blade package.

2. The blade package of claim 1, wherein the means on the base for supporting the blade and assuring that the cutting edge on the blade will not become dulled by inadvertent contact with the base during shipment, storage or handling of the blade package, comprises an upstanding pin on the base, and the blade having a hole formed therein to receive the pin.

3. The blade package of claim 2, wherein the hole in the blade is disposed between the tip of the blade and the forward portion of the slot in the blade.

4. The blade package of claim 2, wherein the blade further has a rear portion, and wherein the base has a rear end wall having a notch formed therein and receiving the rear portion of the blade.

5. The blade package of claim 1, wherein the film is transparent so that the blade is visible in the blade package.

6. The blade package of claim 1, further including a tab on the film, such that the tab may be gripped to rupture the frangible portion of the film and lift it up and away from the base to provide access to the blade.

7. The blade package of claim 2, wherein the base has a peripheral rim, and wherein the blade is disposed on the base below the rim.

8. The blade package of claim 2, wherein the base has a bottom wall formed with an elevated cored-out portion supporting the pin.

9. A blade package for a blade used for surgical purposes, wherein the blade is intended to be mounted on the cleat of a scalpel handle, and wherein the blade is provided with a slot having a forward portion and is further provided with a tip and a cutting edge, comprising a base, means on the base for supporting the blade and assuring that the cutting edge on the blade will not become dulled by inadvertent contact with the base during shipment storage or handling of the blade package, and a relatively-thin film secured to the base and covering the blade, the film being provided with at least a frangible portion, such that the film may be torn away or lifted up and away from the base to expose the blade, such that the cleat on the scalpel handle may be inserted into the slot in the blade to mount the blade on the scalpel handle, and such that the blade mounted on the scalpel handle may be lifted out of the base of the blade package, wherein the means on the base for supporting the blade and assuring that the cutting edge on the blade will not become dulled by inadvertent contact with the base during shipment, storage or handling of the blade package, comprises, an upstanding pin on the base, and the blade having a hole formed therein to receive the pin, wherein the blade further has a rear portion, and wherein the base has a rear end wall having a notch formed therein and receiving the rear portion of the blade, further including an interference fit between the pin and the hole, and between the notch and the rear portion of the blade, respectively, such that the blade is received on the base with a "snap" fit.

10. A blade package for a blade used for surgical purposes, wherein the blade is intended to be mounted on the cleat of a scalpel handle, and wherein the blade is provided with a slot having a forward portion and is further provided with a tip and a cutting edge, comprising a base, means on the base for supporting the blade and assuring that the cutting edge on the blade will not become dulled by inadvertent contact with the base during shipment, storage or handling of the blade package, and a relatively-thin film secured to the base and covering the blade, the film being provided with at least a frangible portion, such that the film may be torn away or lifted up and away from the base to expose the blade, such that the cleat on the scalpel handle may be inserted into the slot in the blade to mount the blade on the scalpel handle, and such that the blade mounted on the scalpel handle may be lifted out of the base of the blade package, wherein the base has respective sides which are indented concavely therein and provided with respective serrations, thereby facilitating gripping of the base.

11. A blade package for a blade used for surgical purposes, wherein the blade is intended to be mounted on the cleat of a scalpel handle, and wherein the blade is provided with a slot having a forward portion and is further provided with a tip and a cutting edge, comprising a base, means on the base for supporting the blade and assuring that the cutting edge on the blade will not become dulled by inadvertent contact with the base during shipment, storage or handling of the blade package, and a relatively-thin film secured to the base and covering the blade, the film being provided with at least a frangible portion, such that the film may be torn away or lifted up and away from the base to expose the blade, such that the cleat on the scalpel handle may be inserted into the slot in the blade to mount the blade on the scalpel handle, and such that the blade mounted on the scalpel handle may be lifted out of the base of the blade package, wherein the base has a bottom wall, and wherein a longitudinally-disposed panel depends from the base centrally thereof, such that the panel may be gripped between a person's thumb and forefinger while rupturing the film and subsequently mounting the blade on the cleat of the scalpel handle.

12. The blade package of claim 11, wherein the panel is connected to the bottom wall of the base by a "living" hinge, such that the panel may be folded for compactness in shipping.

13. A blade package for a blade used for surgical purposes, wherein the blade is intended to be mounted on the cleat of a scalpel handle, and wherein the blade is provided with a slot having a forward portion and is further provided with a tip and a cutting edge, comprising a base, means on the base for supporting the blade and assuring that the cutting edge on the blade will not become dulled by inadvertent contact with the base during shipment, storage or handling of the blade package, and a relatively-thin film secured to the base and covering the blade, the film being provided with at least a frangible portion, such that the film may be torn away or lifted up and away from the base to expose the blade, such that the cleat on the scalpel handle may be inserted into the slot in the blade to mount the blade on the scalpel handle, and such that the blade mounted on the scalpel handle may be lifted out of the base of the blade package, wherein the means on the base for supporting the blade and assuring that the cutting edge on the blade will not become dulled by inadvertent contact with the base during shipment, storage or handling of the blade package, comprises an upstanding pin on the base, and the blade having a hole formed therein to receive the pin, wherein the pin on the base is provided with a cap and is further provided with an annular shoulder below the cap, wherein the notch has respective sides, and wherein longitudinally-disposed ridges are formed on the respective sides of the notch, such that the blade may be "snapped" over the annular shoulder on the cap on the pin and over the respective ridges on the sides of the notch, thereby retaining the blade against movement relative to the base in the mutually-perpendicular X-Y-Z planes.

14. A blade package for a blade used for surgical purposes, wherein the blade is intended to be mounted on the cleat of a scalpel handle, and wherein the blade is provided with a slot having a forward portion and is further provided with a cutting edge, comprising a base, means on the base for supporting the blade and assuring that the cutting edge on the blade will not become dulled by inadvertent contact with the base during shipment, storage or handling of the blade package, a relatively-thin film secured to the base and covering the blade, the film being provided with at least a frangible portion, such that the film may be torn away and lifted up and away from the base to expose the blade, such that the cleat on the scalpel handle may be inserted into the slot in the blade to mount the blade on the scalpel handle, and such that the blade mounted on the scalpel handle may be lifted out of the base of the blade package;

wherein the means on the base for supporting the blade and assuring that the cutting edge on the blade will not become dulled by inadvertent contact with the base during shipment, storage or handling of the blade package, comprises an upstanding pin on the base, the blade having a hole formed therein to receive the pin;

wherein the hole in the blade is disposed between the tip of the blade and the forward portion of the slot in the blade;

wherein the blade further has a tip and a rear portion, and wherein the base has a rear end wall having a notch formed thereon and receiving the rear portion of the blade;

further including an interference fit between the pin and the hole, and between the notch and the rear portion of the blade, respectively, such that the blade is received on the base with a "snap" fit;

wherein the film is transparent so that the blade is visible in the blade package; and further including a tab on the frangible portion of the film, such that the tab may be gripped to rupture the frangible portion of the film and lift it up and away from the base to provide access to the blade.

* * * * *